US010952959B2

(12) United States Patent
Sonavane et al.

(10) Patent No.: US 10,952,959 B2
(45) Date of Patent: Mar. 23, 2021

(54) FAST DISINTEGRATING PHARMACEUTICAL COMPOSITION

(71) Applicant: Ferring B.V., Hoofddorp (NL)

(72) Inventors: Ganeshchandra Sonavane, Thane (IN); Daniel Plaksin, Rehovot (IL); Varinder Ahuja, Mumbai-Maharashtra (IN); Parag Lokhande, Thane-Maharashtra (IN); Devendra Kantilal Jain, Maharashtra (IN)

(73) Assignee: FERRING B.V., Hoofddorp (NL)

( * ) Notice: Subject to any disclaimer, the term of this patent is extended or adjusted under 35 U.S.C. 154(b) by 0 days.

(21) Appl. No.: 16/477,127

(22) PCT Filed: Jan. 11, 2018

(86) PCT No.: PCT/EP2018/050635
§ 371 (c)(1),
(2) Date: Jul. 10, 2019

(87) PCT Pub. No.: WO2018/130603
PCT Pub. Date: Jul. 19, 2018

(65) Prior Publication Data
US 2019/0358156 A1    Nov. 28, 2019

(30) Foreign Application Priority Data

Jan. 11, 2017  (IN) .............................. 201711001145

(51) Int. Cl.
| | |
|---|---|
| *A61K 9/00* | (2006.01) |
| *A61K 38/095* | (2019.01) |
| *A61K 9/19* | (2006.01) |
| *A61K 9/20* | (2006.01) |
| *A61K 31/404* | (2006.01) |
| *A61K 31/47* | (2006.01) |
| *A61K 31/4985* | (2006.01) |
| *A61K 31/519* | (2006.01) |

(52) U.S. Cl.
CPC .............. *A61K 9/0056* (2013.01); *A61K 9/19* (2013.01); *A61K 9/205* (2013.01); *A61K 9/2059* (2013.01); *A61K 9/2095* (2013.01); *A61K 31/404* (2013.01); *A61K 31/47* (2013.01); *A61K 31/4985* (2013.01); *A61K 31/519* (2013.01); *A61K 38/095* (2019.01)

(58) Field of Classification Search
None
See application file for complete search history.

(56) References Cited

U.S. PATENT DOCUMENTS

| | | |
|---|---|---|
| 4,780,414 A | 10/1988 | Nimrod et al. |
| 6,509,040 B1 | 1/2003 | Murray et al. |
| 6,761,904 B2 | 7/2004 | Bertelsen et al. |
| 7,229,641 B2 | 6/2007 | Cherukuri |
| 8,691,271 B2 | 4/2014 | Burnett et al. |
| 8,889,610 B2 | 11/2014 | Labeque et al. |
| 8,900,629 B2 | 12/2014 | Rajewski et al. |
| 8,940,295 B2 | 1/2015 | Sidhu et al. |
| 8,946,153 B2 | 2/2015 | Gupta et al. |
| 9,096,335 B2 | 8/2015 | Ahuja et al. |
| 9,731,018 B2 | 8/2017 | Ahuja et al. |
| 10,023,335 B2 | 7/2018 | Gupta et al. |
| 10,086,078 B2 | 10/2018 | Ahuja et al. |
| 10,512,695 B2 | 12/2019 | Ahuja et al. |
| 2003/0118653 A1 | 6/2003 | Chen et al. |
| 2004/0228919 A1 | 11/2004 | Houghton et al. |
| 2005/0074489 A1 | 4/2005 | Gonzales et al. |
| 2005/0136096 A1 | 6/2005 | Davidson |
| 2005/0136112 A1 | 6/2005 | Gonzales et al. |
| 2005/0191349 A1 | 9/2005 | Boehm et al. |
| 2005/0232990 A1 | 10/2005 | Boehm et al. |
| 2006/0292099 A1 | 12/2006 | Milburn et al. |
| 2009/0004250 A1 | 1/2009 | Gonda |
| 2009/0047330 A1 | 2/2009 | Bangalore |
| 2009/0047350 A1 | 2/2009 | Bangalore |
| 2009/0060993 A1 | 3/2009 | Schwarz et al. |
| 2009/0280160 A1 | 11/2009 | Monteith et al. |
| 2009/0280172 A1 | 11/2009 | Carreno-Gomez |
| 2009/0325861 A1* | 12/2009 | Goodheart .............. A61L 15/46 514/1.1 |
| 2011/0229573 A1 | 9/2011 | Tian |
| 2011/0250256 A1 | 10/2011 | Hyun-Oh et al. |
| 2012/0076858 A1 | 3/2012 | Kolter et al. |
| 2012/0219604 A1* | 8/2012 | Kim ...................... A61K 36/25 424/400 |

(Continued)

FOREIGN PATENT DOCUMENTS

| | | |
|---|---|---|
| CN | 103211801 A | 7/2013 |
| CN | 104000800 A | 8/2014 |

(Continued)

OTHER PUBLICATIONS

CN105663096A, published Jun. 15, 2016, machine translation. (Year: 2016).*
Mitali, World Journal of Pharmaceutical Research, vol. 2, Issue 3, 558-577, 2013. (Year: 2013).*
Bandari et al., "Orodispersible tablets: An overview," Asian Journal of Pharmaceutics (Jan. 2008), pp. 2-11.
Fu et al., "Orally Fast Disintegrating Tablets: Developments, Technologies, Taste-Masking and Clinical Studies," Critical Reviews in Therapeutic Drug Carrier Systems, 21(6):433-475 (2004).

(Continued)

*Primary Examiner* — Layla D Berry
(74) *Attorney, Agent, or Firm* — Foley & Lardner LLP (57) ABSTRACT

The subject invention is directed to a pharmaceutical composition comprising an open matrix network incorporating one or more pharmaceutically active ingredients, wherein the open matrix network comprises maltodextrin and hyaluronic acid or a pharmaceutically acceptable salt thereof.

11 Claims, 3 Drawing Sheets

(56) References Cited

U.S. PATENT DOCUMENTS

| | | |
|---|---|---|
| 2013/0039981 A1 | 2/2013 | Cherurkuri |
| 2013/0101636 A1 | 4/2013 | Lang |
| 2014/0080353 A1* | 3/2014 | Ku .................... H01R 13/7175 |
| | | 439/490 |
| 2014/0166024 A1 | 6/2014 | Davidson et al. |
| 2014/0271923 A1 | 9/2014 | Reid |
| 2015/0038594 A1 | 2/2015 | Borges et al. |
| 2015/0274765 A1 | 10/2015 | Kumar et al. |
| 2017/0304456 A1 | 10/2017 | Ahuja et al. |
| 2018/0297728 A1 | 10/2018 | Gupta et al. |
| 2018/0369392 A1 | 12/2018 | Ahuja et al. |

FOREIGN PATENT DOCUMENTS

| | | |
|---|---|---|
| CN | 104523657 A | 4/2015 |
| CN | 104958279 A | 10/2015 |
| CN | 105663096 A | 6/2016 |
| EP | 1 803 446 A1 | 7/2007 |
| EP | 2 942 058 A1 | 11/2015 |
| IN | 2010MU02146 | 10/2010 |
| KR | 2016-0030729 A | 3/2016 |
| WO | WO-00/61117 A1 | 10/2000 |
| WO | WO-02/05820 A1 | 1/2002 |
| WO | WO-03/094885 A1 | 11/2003 |
| WO | WO-03/094886 A2 | 11/2003 |
| WO | WO-2004/041153 A2 | 5/2004 |
| WO | WO-2008/027904 A2 | 3/2008 |
| WO | WO-2008/065144 A2 | 6/2008 |
| WO | WO-2009/063291 A1 | 5/2009 |
| WO | WO-2011/120903 A2 | 10/2011 |
| WO | WO-2011/120904 A2 | 10/2011 |
| WO | WO-2013/037708 | 3/2013 |
| WO | WO-2013/037708 A1 | 3/2013 |
| WO | WO-2013/063510 A1 | 5/2013 |
| WO | WO-2013/136346 A2 | 9/2013 |
| WO | WO-2014/058742 A1 | 4/2014 |
| WO | WO-2014/079922 A1 | 5/2014 |
| WO | WO-2014/119984 A2 | 8/2014 |
| WO | WO-2014/166994 A1 | 10/2014 |
| WO | WO-2015/155307 A1 | 10/2015 |

OTHER PUBLICATIONS

Mohd et al., "Tensile Strength and Bonding in Compacts: A Comparison of Diametral Compression and Three-Point Bending for Plastically Deforming Materials," Drug Development and Industrial Pharmacy, (2002) 28(7):809-813.

Morjaria et al., "In Vitro Release of Nicotine From Chewing Gum Formulations," Dissolution Technologies, pp. 12-15 (May 2004).

Seager, "Drug-delivery Products and the Zydis Fast-dissolving Dosage Form," J. Pharm. Pharmacol. 50:375-382 (1998).

* cited by examiner

FAST DISINTEGRATING PHARMACEUTICAL COMPOSITION

CROSS-REFERENCE TO RELATED APPLICATIONS

The present application is the U.S. National Stage of International Application No. PCT/EP2018/050635, filed Jan. 11, 2018, and claims priority to Indian Patent Application No. 201711001145, filed Jan. 11, 2017.

FIELD OF THE INVENTION

The subject invention relates to fast disintegrating pharmaceutical compositions, to methods of making them and to their use in the treatment and prophylaxis of diseases in mammals, particularly humans.

BACKGROUND OF THE INVENTION

Fast disintegrating pharmaceutical dosage forms which are designed to release an active ingredient in the oral cavity are well known and can be used to deliver a wide range of drugs (*Critical Reviews in Therapeutic Drug Carrier Systems*, 21(6):433-475 (2004); Seager H. (1998), *J. Phar. Pharmacol* 50:375-382; Bandari et al. (January 2008), *Asian Journal of Pharmaceutics* 2-11).

In a fast disintegrating dosage form, a drug is physically trapped in a matrix composed of e.g. mannitol and fish gelatin (EP 1501534; EP 1165053), modified starch (U.S. Pat. No. 6,509,040), pullulan in combination with an amino acid (EP 1803446), or maltodextrin in combination with sorbitol (US 2004/0228919). A solution or suspension of the drug and the matrix (carrier) material may be filled into blister cavities, frozen and thereafter lyophilized. However, some of these dosage forms produced in this manner are fragile and brittle, have limited physical strength, and cannot withstand any pressure. In addition, dosage units so produced are difficult to pack and unpack.

In a second generation of fast disintegrating dosage forms, drugs are physically trapped in a matrix composed of levan (WO 2011/120904), or levan in combination with inulin (WO 2013/037708). These dosage forms show an improved tensile strength while maintaining a rapid disintegrating rate.

The subject invention now provides for an improved third generation fast disintegrating dosage form based on a matrix comprising a combination of maltodextrin and hyaluronic acid (HA) or a pharmaceutically acceptable salt thereof.

SUMMARY OF THE INVENTION

The subject invention provides new fast disintegrating oral pharmaceutical compositions typically in a unit dosage form, typically oral lyophilisates (also named orally disintegrating tablets). Fast disintegrating dosage forms of the invention have relatively high tensile strength (i.e. force required to break a tablet in a three-point bending test) on the one hand and a fast disintegration time on the other hand. This relatively high tensile strength permits, amongst others, to easily remove the composition from its container, typically a blister pack, without disintegration. The unit dosage form of the invention can typically be handled in a manner similar to that of a conventional compressed tablet, with disintegration occurring only upon contact with an aqueous liquid, such as saliva within the mouth.

The subject invention thus provides a pharmaceutical composition comprising an open matrix network carrying a pharmaceutically active ingredient, wherein the open matrix network comprises maltodextrin and HA or a pharmaceutically acceptable salt thereof.

The subject invention further provides a pharmaceutical composition comprising a matrix carrying a pharmaceutically active ingredient, the matrix rapidly disintegrating upon contact with an aqueous medium, said matrix comprising maltodextrin and HA or a pharmaceutically acceptable salt thereof.

The pharmaceutical composition of the invention is unique in that it has a high tensile strength, on the one hand, and exhibits a rapid disintegration in an aqueous medium, on the other hand.

The relatively high tensile strength permits the handling of the dosage form in a manner similar to that of a regular compressed tablet including, in particular, removal from a package in which they are held, e.g. a blister pack, without risk of damaging the dosage form between the fingers. Notwithstanding this tensile strength, the composition of the invention disintegrates rapidly when contacted with an aqueous medium, in particular the composition rapidly disintegrates when taken orally. The disintegration in an aqueous medium, such as in the oral cavity upon ingestion (where the composition disintegrates upon contact with saliva), is typically within 30 seconds, and more typically within 10 seconds, at times within 9, 8, 7, 6, 5, 4, 3, 2 or even 1 second.

The pharmaceutical composition of the invention typically has a tensile strength of at least 0.1 N/mm$^2$ and preferably a rapid disintegration rate such that the composition disintegrates in an aqueous medium within 30 seconds, at times within 10 seconds and even within 9, 8, 7, 6, 5, 4, 3, 2, or 1 second.

The pharmaceutical composition of the invention may be obtained by subliming the solvent (e.g. water), for example in a freeze drying process, from a liquid preparation that comprises the active ingredient(s) and the matrix forming agents in solution or suspension. According to one embodiment, unit dosage quantities of the liquid preparation are introduced into depressions and sublimation is then carried out, thereby obtaining (after sublimation of the solvent) a pharmaceutical composition in a unit dosage form. The depressions may be those of an open blister pack, and following the sublimation step (and thereby the formation of the solid unit dosage form of the composition in the depression), a sealing film or foil is placed over the depressions to form a sealed blister pack.

The invention further provides a process for preparing a pharmaceutical composition that comprises subliming the solvent from a liquid preparation comprising one or more pharmaceutically active ingredients, maltodextrin and HA or a pharmaceutically acceptable salt thereof in a solvent.

The invention also provides a process for the preparation of a pharmaceutical composition comprising (a) preparing a preparation comprising maltodextrin, hyaluronic acid or a pharmaceutically acceptable salt thereof and one or more active ingredients in a solvent; (b) freezing said preparation; (c) subliming the solvent from the frozen preparation, wherein the pharmaceutical composition so obtained is a fast-disintegrating dosage form which disintegrates within 30 seconds upon contact with an aqueous medium.

FIGURES

FIG. 1 shows the tensile strength and in vitro disintegration time of several lyophilisates based on the following combinations of matrix forming agents:

a) Maltodextrin+sodium hyaluronate (example 1)
b) Maltodextrin+sodium hyaluronate (example 2)
c) Levan+sodium hyaluronate (example 3)
d) Pullulan+sodium hyaluronate (example 4)
e) Maltodextrin+levan (example 5)
f) Maltodextrin+pullulan (example 6)

DETAILED DESCRIPTION OF THE INVENTION

Figure 1:
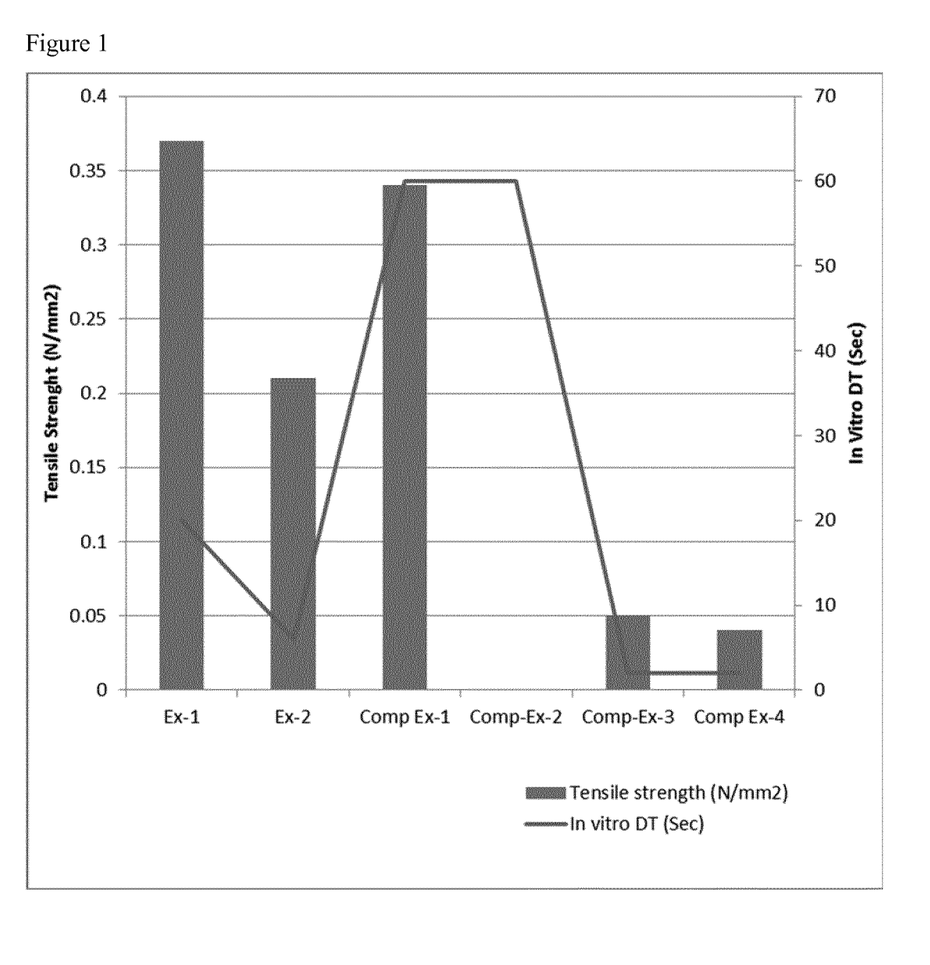
Figure 2:
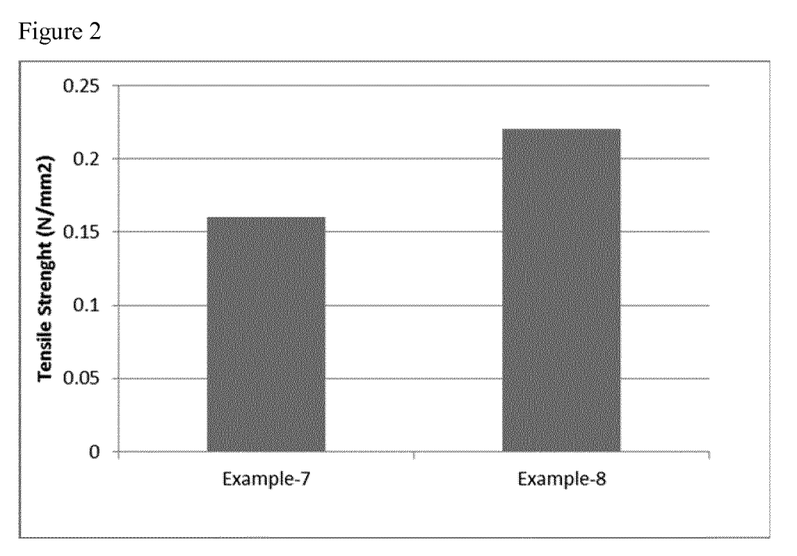
FIG. 2 shows the tensile strength of:
a) A desmopressin acetate formulation (example 7) of the invention; and
b) A montelukast formulation (example 8) of the invention.
Figure 3:
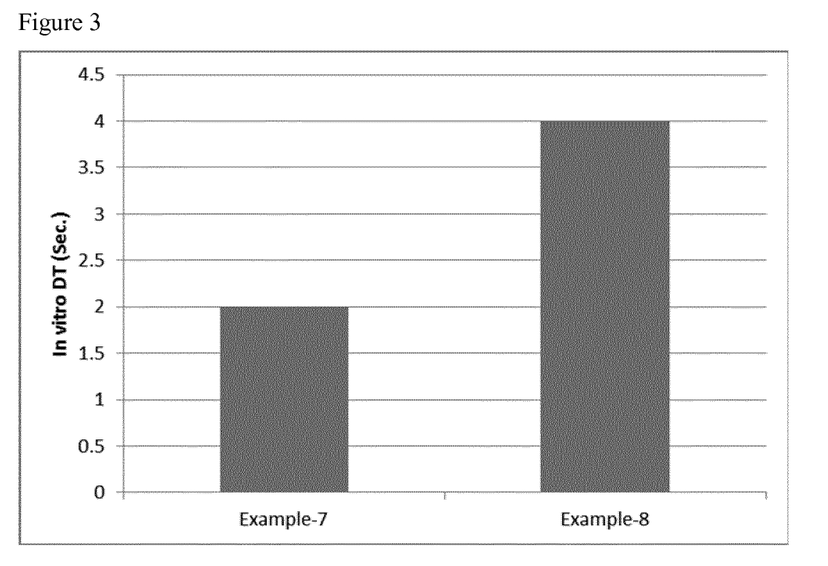
FIG. 3 shows the in vitro disintegration time of
a) A desmopressin formulation (example 7) of the invention; and
b) A montelukast formulation (example 8) of the invention.
Figure 4:
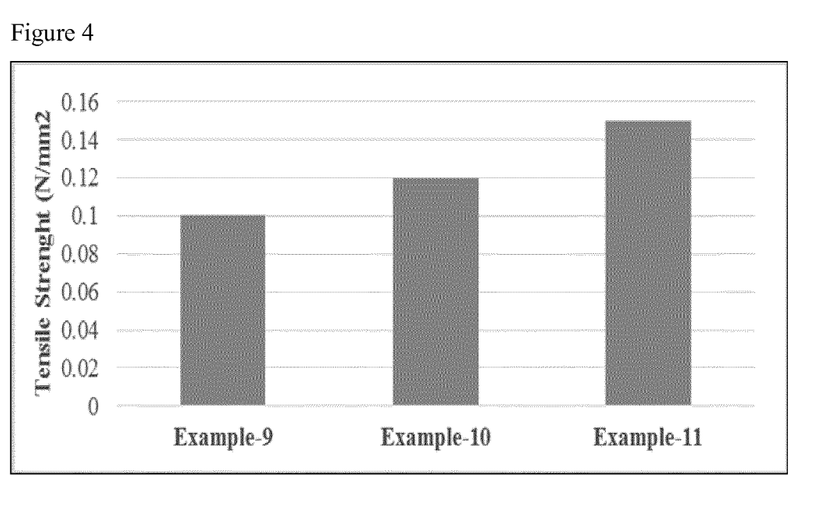
FIG. 4 shows the tensile strength of:
a) A sildenafil citrate formulation (example 9) of the invention;
b) A silodosin formulation (example 10) of the invention; and
c) A tadalafil formulation (example 11) of the invention
Figure 5:
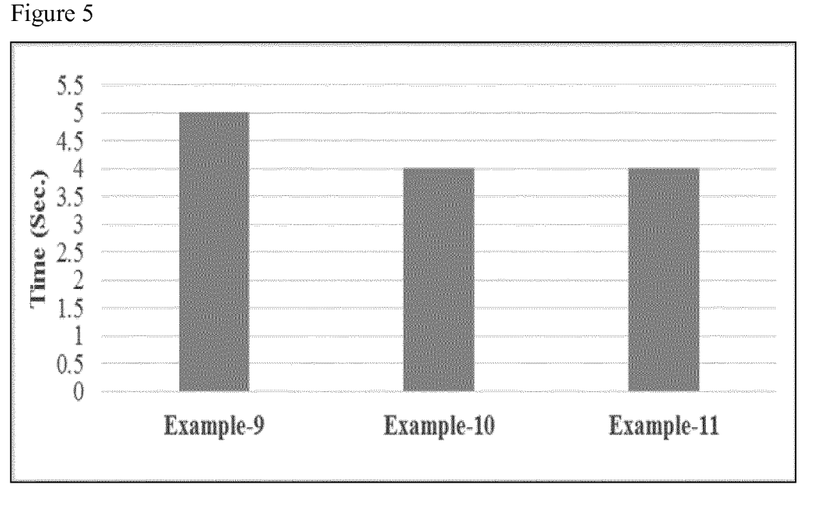
FIG. 5 shows the in vitro disintegration time of
a) A sildenafil citrate formulation (example 9) of the invention;
b) A silodosin formulation (example 10) of the invention; and
c) A tadalafil formulation (example 11) of the invention

The subject invention provides a fast-disintegrating, typically orodispersible, pharmaceutical composition, usually prepared and provided in unit dosage form, typically an oral lyophilisate, comprising one or more active ingredients and two or more excipients. The excipients are at least maltodextrin and hyaluronic acid or a pharmaceutically acceptable salt thereof.

The following are some of the terms used above and below in this patent specification and claims:

The terms "active ingredient" or "pharmaceutically active ingredient" will be used interchangeably herein.

The term "pharmaceutical composition" and "composition" are interchangeably used herein to refer to a pharmaceutical composition of the invention.

The term "unit dosage form" or "dosage form" will be used herein to refer to said composition which is formulated with an amount of a pharmaceutically active ingredient in a dose for administration as a single dose to a target individual. The unit dosage form may be adapted, depending on the nature of the active ingredient, the indication, the disease stage and various other factors known per se for once, twice, thrice or any other number of daily administrations.

The term "carrying" when defining the relation between a matrix or open matrix network and an active ingredient should be understood to encompass any manner by which the matrix holds, contains or incorporates an amount of the active ingredient and releases it to the aqueous medium upon disintegration of the matrix.

The term "matrix" should be understood to denote a solid carrier medium for an active ingredient. The matrix comprises two or more excipients. The excipients that form the matrix may be referred to herein, at times, as "matrix forming agents" and each of said agents as "matrix forming agent".

The term "an open matrix network" should be understood to encompass a matrix of water-soluble or water-dispersible carrier material (matrix-forming agent(s)) having interstices dispersed throughout. The matrix rapidly disintegrates upon contact with an aqueous solution, such as saliva.

In one embodiment, maltodextrin and hyaluronic acid or a pharmaceutically acceptable salt thereof are the sole matrix forming agents in the composition.

In another embodiment, one or more secondary matrix forming agents may additionally be present in the composition. Non-limiting examples of sugars, sugar alcohols, monosaccharides, disaccharides, trisaccharides, polysaccharides, proteins, amino acids, gums and the like, which are useful as secondary matrix forming agents, include without limitation, mannitol, trehalose, raffinose, inositol, pullulan, sucrose, lactose, dextrose, erythritol, xylitol, lactitol, maltitol, isomalt, alanine, arginine, threonine, glycine, cysteine, serine, histidine, valine, proline, lysine, asparagine, glutamine, ribose, glucose, galactose, fructose, maltose, maltotriose, guar gum, xanthan gum, tragacanth gum, veegum and so forth.

Generally, apart from the active ingredient, the balance of the composition can be matrix. Thus the combined percentage of the matrix of maltodextrin and hyaluronic acid or a pharmaceutically acceptable salt thereof can approach 100%.

In one embodiment, maltodextrin and hyaluronic acid or a pharmaceutically acceptable salt thereof are the matrix forming agents, constituting 10 to 99.99% of the total weight of the matrix or open matrix network, including any material carried, i.e. held, contained or incorporated therein, such as active ingredient(s), secondary matrix-forming agent(s) etc. In another embodiment, maltodextrin constitutes 10 to 99% and hyaluronic acid or a pharmaceutically acceptable salt thereof constitutes 0.99 to 5% of the total weight of the matrix or open matrix network. In yet another embodiment, maltodextrin constitutes 40 to 99% and hyaluronic acid or a pharmaceutically acceptable salt thereof constitutes 0.99 to 5% of the total weight of the matrix or open matrix network. In yet another embodiment, maltodextrin constitutes 50 to 98% and hyaluronic acid or a pharmaceutically acceptable salt thereof constitutes 0.99 to 3% of the total weight of the matrix or open matrix network.

In embodiments, the composition of the invention does not contain one or more excipients selected from the group consisting of fish gelatin, modified starch, pullulan in combination with an amino acid, and maltodextrin in combination with sorbitol.

"Disintegration Time" should be understood to mean the time needed for the composition of the invention to disintegrate in an aqueous solution or aqueous medium such as saliva within the oral cavity.

"Oral dissolving time" as used herein should be understood to mean the time needed for the composition of the invention to dissolve in the oral cavity.

"Rapid/Fast disintegration" as used herein should be understood to encompass disintegration of the composition of the invention in an aqueous medium within 30 seconds, typically within 10 seconds and at times even within 9, 8, 7, 6, 5, 4, 3, 2 or 1 second.

Examples of an aqueous medium as used herein are water or a buffer (e.g. potassium dihydrogen phosphate, dipotassium hydrogen phosphate, sodium hydrogen phosphate) or artificial saliva as described by Morjaria et. al (May 2004), *Dissolution Technologies* 12-15. For the purpose of determining disintegration/dissolution times, an "aqueous medium" as used herein is purified water Saliva as used herein refers to the saliva in the oral cavity of a mammal, in particular a human.

"Tensile strength" as used herein should be understood to be the force required to break a tablet, which is measured by the three-point bending test, wherein the tablet is subjected to a bending stress (Mohd et al. (2002), Drug Development and Industrial Pharmacy 28(7):809-813).

In one embodiment, a pharmaceutical composition of the invention has a tensile strength of at least 0.1 N/mm².

It is envisaged that a pharmaceutical composition of the invention has a rapid disintegration rate such that the composition disintegrates in an aqueous medium within 30 seconds, typically within 10 seconds.

In one embodiment, a pharmaceutical composition of the invention has a tensile strength of at least 0.2 N/mm² and a rapid disintegration rate such that the composition disintegrates in an aqueous medium within 30 seconds, typically within 10 seconds.

In another embodiment, the invention provides a pharmaceutical composition comprising a pharmaceutically active ingredient, having a tensile strength of at least 0.3 N/mm² and a rapid disintegration rate such that the composition disintegrates in an aqueous medium within 30 seconds, typically within 10 seconds.

The matrix or open matrix network comprising maltodextrin and hyaluronic acid or a pharmaceutically acceptable salt thereof generally is of a single-phase structure. This is opposed to a composition having a two-phase or multiple-phase structure wherein, e.g., maltodextrin is in one phase and hyaluronic acid or a pharmaceutically acceptable salt thereof is in another phase.

The open matrix network enables a liquid to enter the dosage form through the interstices and permeate through its interior. Permeation by aqueous media (such as saliva, water, etc.) exposes the carrier material of both the interior and exterior of the dosage form to the action of the aqueous media whereby the network of carrier material rapidly disintegrates.

The open matrix structure is of a porous nature and enhances disintegration of the dosage form as compared with ordinary solid shaped pharmaceutical dosage forms such as (granulated and compressed) tablets, pills, capsules, suppositories and pessaries. Rapid disintegration results in rapid release of the active ingredient carried by the matrix.

In the subject invention, the first carrier material of the matrix or open matrix network is maltodextrin. Maltodextrin is a polysaccharide that is currently mainly used as a food additive. It is produced from starch by partial hydrolysis. Maltodextrin is easily digestible, being absorbed as rapidly as glucose. Maltodextrin consists of D-glucose units connected in chains of variable length. The glucose units are primarily linked with $\alpha(1 \to 4)$ glycosidic bonds. Maltodextrin is typically composed of a mixture of chains that vary from three to 17 glucose units in length.

α-1,4
2 < n < 20

Maltodextrin in itself, at a concentration from 10 to 30 mg/lyophilisate, is brittle in nature and has a very low tensile strength (i.e. below 0.06 N/mm²).

The second carrier material of the matrix or open matrix network is hyaluronic acid or a pharmaceutically acceptable salt thereof, such as sodium hyaluronate. Hyaluronic acid is a naturally occurring biopolymer consisting of repeating disaccharide units of D-glucuronic acid in β-(1-3) linkage with N-acetyl-D-glucosamine, wherein each disaccharide unit is connected to its adjoining neighbors by β-(1-4) linkages. The salt sodium hyaluronate is found at physiological pH in human and vertebrate joint synovial fluid, connective tissue, vitreous humor of the eye and healthy skin tissue, and is an extracellular secretion product of several bacterial species, particularly of the genus *Streptococcus*.

In the present invention, hyaluronic acid and pharmaceutically acceptable salts thereof, in particular the sodium salt, can be used interchangeably and are collectively abbreviated as HA. In one embodiment, the HA may also be chemically modified, in particular at the hydroxyl and/or carboxyl groups.

The HA used herein can be obtained from commercial sources or can be produced by methods known in the art.

The HA used herein can be obtained from a source selected from the group consisting of a biological source, an in vitro enzymatic synthesis, a chemical synthesis, and combinations of two or more such sources, wherein the biological source is preferably selected from the group consisting of a bacterium, a yeast, a plant, an amphibian, an avian and a mammal.

Preferably, the HA has an average molecular weight in the range from $1 \times 10^4$ to $1 \times 10^7$ dalton, preferably an average molecular weight of $3 \times 10^6 \pm 0.6 \times 10^6$ dalton, when determined in the form of sodium hyaluronate. The average molecular weight refers to the molecular weight as determined on the basis of the intrinsic viscosity and using the Mark-Houwink relation (see, e.g., U.S. Pat. No. 4,780,414, "Properties of the product sodium hyaluronate").

When the HA is obtained from a bacterium, the bacterium is preferably a strain of a genus *Streptococcus*, preferably a *Streptococcus* species selected from the group consisting of *Streptococcus equi, Streptococcus pyogenes, Streptococcus equisimilis, Streptococcus dysgalactiae* and *Streptococcus zooepidemicus*, and/or the *Streptococcus* strain is preferably non-hemolytic and non-pathogenic.

In one embodiment, the HA is thus isolated from the culture broth of a fermented *Streptococcus* strain.

HA may further comprise a chemical modification, wherein the chemical modification preferably comprises a modification selected from the group consisting of addition of sulfate groups, addition of carboxyl groups, addition of hydroxyl groups, addition of acetyl groups, esterification and cross-linking In one embodiment, the hyaluronic acid is chemically cross-linked.

In another embodiment, the hyaluronic acid is complexed with a metal.

In one embodiment, the HA used for forming the composition of the present invention is an aqueous product having an HA concentration in the range of from about 0.8 to about 3.0% w/v, preferably about 1.0% w/v, about 1.2% w/v, or about 2.0% w/v, calculated as sodium hyaluronate.

Sodium hyaluronate alone (i.e. without the addition of maltodextrin) does not form a lyophilisate having a desirable tensile strength.

The pharmaceutical composition of the present invention comprises, in the matrix or open matrix network, one or more pharmaceutically active ingredients. They may e.g. be selected from oligopeptides, polypeptides (proteins), nucleotides, polynucleotides or "small molecules". Non-limiting examples of pharmaceutically active ingredients which can be carried by the matrix or open matrix network of the subject invention are analgesics, alpha blockers, anti-allergy, anti-asthma, (allergic rhinitis, chronic uticaria), anti-inflammatory, antacids, anthelmintics, anti-arrhythmic agents, anti-arthritis, anti-bacterial, anti-anxiety, anti-coagulants, anti-depressants, anti-diabetics, anti-diarrheals, anti-diuretics, anti-epileptics, anti-fungal, anti-gout, anti-hypertensive, anti-incontinence, anti-insomnia, anti-malarials, anti-migraine, anti-muscarinic, anti-neoplastic and immuno-suppressants, anti-protozoal, anti-rheumatics, anti-rhinitis, anti-spasmatic. anti-thyroid, antivirals, anxiolytics, sedatives, hypnotics and neuroleptics, beta-blockers, anti-benign hyperplasia (BHP), cardiac inotropic, corticosteroids, cough suppressants, cytotoxics, decongestants, diabetic gastric stasis, diuretics, enzymes, anti-parkinsonian, gastro-intestinal, histamine receptor antagonists, infertility, endometriosis, hormone replacement therapy, lipid regulating agents, local anesthetics, neuromuscular agents, nitrates and anti-anginal agents, menstrual disorders, motion sickness, anti-pain, anti-nausea, movement disorders, nutritional agents, opioid analgesics, oral vaccines, proteins, peptides and recombinant drugs, prevention of chemotherapy induced and post-operative nausea and vomiting, proton pump inhibitors, schizophrenia, hormones, contraceptives, seizure/panic disorder, sexual dysfunction (male and female), spermicides, stimulants voiding dysfunctions, veterinary medicines and so forth.

Specific non-limiting examples of these active ingredients are:

Alfa blockers: Tamsulosine

Analgesics and anti-inflammatory agents: aspirin, aloxiprin, auranofin, azapropazone, benorylate, diflunisal, etodolac, fenbufen, fenoprofen calcium, flurbiprofen, ibuprofen, indomethacin, ketoprofen, meclofenamic acid, mefenamic acid, nabumetone, naproxen, oxaprozin, oxyphenbutazone, phenylbutazone, piroxicam, sulindac, paracetamol.

Antacids: aluminum hydroxide, magnesium carbonate, magnesium trisilicate, hydrotalcite, dimethicone.

Antihelmintics: albendazole, bephenium hydroxynaphthoate, cambendazole, dichlorophen, ivermectin, mebendazole, oxamniquine, oxfendazole, oxantel embonate, praziquantel, pyrantel embonate, thiabendazole.

Anti-allergic: des loratidine, loratidine, Montelukast, Montelukast sodium, Cetirizin, Fexofenadin, Ebastine.

Anti-arrhythmic agents: amiodarone HCl, disopyramide, flecainide acetate, quinidine sulphate.

Anti-bacterial agents: benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim.

Anti-coagulants: dicoumarol, dipyridamole, nicoumalone, phenindione.

Anti-depressants: amoxapine, ciclazindol, maprotiline HCl, mianserin HCl, nortriptyline HCl, trazodone HCl, trimipramine maleate.

Anti-diabetics: acetohexamide, chlorpropamide, glibenclamide, gliclazide, glipizide, tolazamide, tolbutamide.

Anti-diarrheals: atropine sulphate, codeine phosphate, cophenotrope, difenoxin, loperamide hydrochloride, suphasolazine, mesalazine, olsalazine, corticosteroids, prednisolone.

Anti-diuretics: desmopressin, desmopressin acetate.

Anti-epileptics: beclamide, carbamazepine, clonazepam, ethotoin, methoin, methsuximide, methylphenobarbitone, oxcarbazepine, paramethadione, phenacemide, phenobarbitone, phenytoin, phensuximide, primidone, sulthiame, valproic acid.

Anti-fungal agents: amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid.

Anti-gout agents: allopurinol, probenecid, sulphinpyrazone.

Anti-hypertensive agents: amlopidine, benidipine, darodipine, dilitazem HCl, diazoxide, felodipine, guanabenz acetate, indoramin, isradipine, minoxidil, nicardipine HCl, nifedipine, nimodipine, phenoxybenzamine HCl, prazosin HCl, reserpine, terazosin HCl.

Anti-insomnia: Zolpidem

Anti-malaria: amodiaquine, chloroquine, chloroproguanil HCl, halofantrine HCl, mefloquine HCl, proguanil HCl, pyrimethamine, quinine sulphate.

Anti-migraine agents: rizatriptan, dihydroergotamine mesylate, ergotamine tartrate, methysergide maleate, pizotifen maleate, sumatriptan succinate, caffeine.

Anti-muscarinic agents: oxybutinin, tolterodin, atropine, benzhexol HCl, biperiden, ethopropazine HCl, hyoscine butyl bromide, hyoscyamine, mepenzolate bromide, orphenadrine, oxyphencylcimine HCl, tropicamide.

Anti-neoplastic agents and Immunosuppressants: aminoglutethimide, amsacrine, azathioprene, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone.

Anti-protozoal agents: benznidazole, clioquinol, decoquinate, diiodohydroxyquinoline, diloxanide furcate, dinitolmide, furzolidone, metronidazole, nimorazole, nitrofurazone, ornidazole, tinidazole.

Anti-rheumatics: ibuprofen, aceclofenac, acemetacin, azapropazone, diclofenac sodium, diflunisal, etodolac, ketoprofen, indomethacin, mefenamic acid, naproxen, piroxicam, aspirin, benorylate, auranofin, penicillamine.

Anti-rhinitis, anti-uticaria: Cetirizin, fexofenadin, ebastine, loratidin, montelukast Anti-spasmatic: phloroglucinol anhydre Anti-thyroid agents: carbimazole, propylthiouracil.

Antivirals: acyclovir, amantadine hydrochloride, famciclovir, zidovadine, didanosine, zalcitabine, foscarnet sodium.

Anxiolytic, sedatives, hypnotics and neuroleptics: alprazolam, amylobarbitone, barbitone, bentazepam, bromazepam, bromperidol, brotizolam, butobarbitone, carbromal, chlordiazepoxide, Chlorpheniramine, chlormethiazole, chlorpromazine, clobazam, clonazepan, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine phenylephrine, pimozide, prochlorperazine, pseudoephedrineHCL, sulpride, temazepam, thioridazine, triazolam, zopiclone.

β-Blockers: acebutolol, alprenolol, atenolol, labetalol, metoprolol, nadolol, oxprenolol, pindolol, propanolol.

Cardiac inotropic agents: amrinone, digitoxin, digoxin, enoximone, lanatoside C, medigoxin.

Contraceptives: clomiphene citrate, danazol, desogestrel, ethinyloestradiol, ethynodiol, ethynodiol diacetate, levonorgestrel, medroxyprogesterone acetate, mestranol, methyltestosterone, norethisterone, norethisterone enanthate, norgestrel, estradiol, conjugated estrogens, dydrogesterone, progesterone, stanozolol, stilboestrol, testosterone, tibolone.

Corticosteroids: beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone.

Cough suppressants: codeine phosphate dexomethorphan, guaifenesin, pholcodine, diamorphine, methadone.

Cytotoxics: ifosfamide, chlorambucil, melphalan, busulphan, cytotoxic antibodies, doxorubicin, epirubicin, plicamycin, bleomycin, methotrexate, cytarabine, fludarabine, gencitabine, fluorouracil, mercaptopurine, thioguanine, vincristine, vinblastine, vindesine, etoposide.

Decongestants: pseudo ephedrine hydrochloride.

Diuretics: acetazolamide, amiloride, bendrofluazide, bumetanide, chlorothiazide, chlorthalidone, ethacrynic acid, frusemide, metolazone, spironolactone, triamterene.

Enzymes: pancreatin, pepsin, lipase.

Epilepsy: Gabapentin

Anti-parkinsonian agents: bromocriptine mesylate, lysuride maleate, selegiline, para-fluoroselegiline, lazabemide, rasagiline, 2-BUMP [N-(2-butyl)-N-methylpropargylamine], M-2-PP [N-methyl-N-(2-pentyl)-propargylamine], MDL-72145 [beta-(fluoromethylene)-3,4-dimethoxy-benzeneethanamine], mofegiline, apomorphine, N-propylnoraporphine, cabergoline, metergoline, naxagolide, pergolide, piribedil, ropinirole, terguride, quinagolide.

Gastro-intestinal agents: bisacodyl, cimetidine, cisapride, diphenoxylate HCl, domperidone, metoclopramide, famotidine, loperamide, mesalazine, nizatidine, esomeprazole, metopimazine, pantoprazole, ondansetron HCl, Granisetron, tropisetron, dolasetron, ranitidine HCl, sulphasalazine. Lanzoprazole, Histamine Receptor Antagonists: acrivastine, astemizole, cinnarizine, cyclizine, cyproheptadine HCl, dimenhydrinate, flunarizine HCl, loratadine, meclozine HCl, oxatomide, terfenadine, triprolidine.

Hormones: Human Growth hormone (HGH), Follicle Stimulating Hormone (FSH), Gonadotropin-releasing hormone (GnRH) Agonist or antagonist, nafarelin Triptorelin, cetrorelix, atosiban.

Hormone replacement therapy: dydrogesterone

Hypertension: Enalapril

Lactation: Oxytocin, oxytocin agonists

Lipid regulating agents: bezafibrate, clofibrate, fenofibrate, gemfibrozil, probucol.

Local anaesthetics: amethocaine, amylocaine, benzocaine, bucricaine, bupivacaine, butacaine, butanilicaine, butoxycaine, butyl aminobenzoate, carticaine, chloroprocaine, cinchocaine, clibucaine, clormecaine, coca, cocaine, cyclomethycaine, dimethisoquin, diperodon, dyclocaine, ethyl chloride, ethyl p-piperidinoacetylaminobenzoate, etidocaine, hexlcaine, isobutamben, ketocaine, lignocaine, mepivacaine, mepryl caine, myrtecaine, octacaine, oxethazaine, oxybuprocaine, parethoxycaine, pramoxine, prilocaine, procaine, propranocaine, propoxycaine, proxymetacaine, ropivacaine, tolycaine, tricaine, trimecaine, vadocaine.

Motion sickness: diphenhydramine

Neuro-muscular agents: pyridostigmine.

Nitrates and other anti-anginal agents: amyl nitrate, glyceryl trinitrate, isosorbide dinitrate, isosorbide mononitrate, pentaerythritol tetranitrate.

Nutritional agents: betacarotene, vitamins, such as vitamin A, vitamin $B_2$, vitamin D, vitamin E, vitamin K, minerals.

Opioid analgesics: codeine, dextropropyoxyphene, diamorphine, dihydrocodeine, meptazinol, methadone, morphine, nalbuphine, pentazocine.

Oral vaccines: to prevent or reduce the symptoms of diseases such as Influenza, Tuberculosis, Meningitis, Hepatitis, Whooping Cough, Polio, Tetanus, Diphtheria, Malaria, Cholera, Herpes, Typhoid, HIV, AIDS, Measles, Lyme disease, Traveller's Diarrhea, Hepatitis A, B and C, Otitis Media, Dengue Fever, Rabies, Parainfluenza, Rubella, Yellow Fever, Dysentery, Legionnaires Disease, Toxoplasmosis, Q-Fever, Haemorrhegic Fever, Argentina Haemorrhegic Fever, Caries, Chagas Disease, Urinary Tract Infection caused by *E. coli*, Pneumococcal Disease, Mumps, Chikungunya, Hayfever, Asthma, Rheumatoid Arthritis, Carcinomas, Coccidiosis, Newcastle Disease, Enzootic pneumonia, Feline leukemia, Atrophic rhinitis, Erysipelas, Foot and Mouth disease and Swine pneumonia, or to prevent or reduce the symptoms of diseases caused by *Vibrio* species, *Salmonella* species, *Bordetella* species, *Haemophilus* species, *Toxoplasmosis gondii*, *Cytomegalovirus*, *Chlamydia* species, *Streptococcal* species, Norwalk Virus, *Escherichia coli*, *Helicobacter pylori*, Rotavirus, *Neisseria gonorrhae*, *Neisseria meningiditis*, Adenovirus, Epstein Barr Virus, Japanese Encephalitis Virus, *Pneumocystis carini*, Herpes simplex, *Clostridia* species, Respiratory Syncytial Virus, *Klebsiella* species, *Shigella* species, *Pseudomonas aeruginosa*, Parvovirus, *Campylobacter* species, *Rickettsia* species, *Varicella zoster*, *Yersinia* species, Ross River Virus, J.C. Virus, *Rhodococcus equi, Moraxella catarrhalis, Borrelia burgdorferi* and *Pasteurella haemolytica*, BCG.

Voiding dysfunctions: Tamsulosine, trospium chloride, tolterodine, oxybutinin

Proteins, peptides and recombinant drugs: recombinant hormones and iso-hormones, recombinant cytokines, recombinant plasminogens, TNF receptor fusion protein, monoclonal antibodies, nucleic acids, antisense oligonucleotides, oligonucleotides, glycoproteins and adhesion molecules, Calcitonin, octreotide, insulin and insulin analogs, etanercept, pegfilgrastim, liraglutide, bivalirudin, nesiritide, ceruletide, bentiromide, exenatide, gonadorelin, enfuvirtide, vancomycin, icatibant, secretin, leuprolide, glucagon recombinant, oxytocin, sermorelin, gramicidin D, Insulin recombinant, capreomycin, vasopressin, cosyntropin, bacitracin, abarelix, vapreotide, thymalfasin, mecasermin, teriparatide, corticotropin, pramlintide.

Veterinary Arthiritis: Tepoxalin

Schizophrenia: Olanzapine, Nicergoline

Sexual dysfunction: Cabergolin, oxytocin, tadalafil, sildenafil, vardenafil

Spermicides: nonoxynol 9.

Stimulants: amphetamine, dexamphetamine, dexfenfluramine, fenfluramine, mazindol, pemoline.

In a specific, non-limiting embodiment, the active ingredient is desmopressin or desmopressin acetate. In this embodiment the dosage form can be used in voiding postponement or in the treatment or prevention of incontinence, primary nocturnal enuresis (PNE), nocturia, nocturnal polyuria or central diabetes insipidus. In one embodiment, the amount of desmopressin acetate in the composition is at least 1% w/w. In another embodiment, the amount of desmopressin acetate in the composition is at least 0.9% w/w.

In a specific, non-limiting embodiment, the active ingredient is montelukast or montelukast sodium. In this embodiment, the dosage form can be used in the treatment of asthma, acute prevention of exercise-induced bronchoconstriction or allergic rhinitis. In one embodiment, the amount of montelukast sodium in the composition is at least 50% w/w. In another embodiment, the amount of montelukast sodium in the composition is at least 40% w/w.

A pharmaceutical dosage form of the invention disintegrates, thereby releasing the active ingredient, upon contact with a fluid (an aqueous medium such as saliva).

Typically, a pharmaceutical dosage form of the invention is an orodispersible pharmaceutical dosage form which disintegrates in the mouth within 30 seconds, typically within 10 seconds.

The term "orodispersible" as used herein should be understood to encompass a solid dosage form which disintegrates in the mouth within 30 seconds. In further embodiments, the orodispersible dosage form disintegrates in the mouth within 10, 9, 8, 7, 6, 5, 4, 3, 2, or even within 1 second.

A suitable route of administration for the dosage form of the subject invention is oral administration including buccal and sublingual administration. In a specific embodiment, the dosage form is administered sublingually. Dosage forms of the invention may also be placed on the tongue or against the cheek or gingiva.

Pharmaceutical dosage forms of the present invention are adapted to supply the active ingredient to e.g. the oral cavity. The active may be absorbed across the mucosa at the site of administration, e.g. sublingual mucosa, and/or otherwise, in the case of oral administration, from the oral cavity (e.g. across the buccal and/or gingival mucosa) and/or from the gastrointestinal tract for systemic distribution.

The exact dose and regimen of administration of the dosage form will necessarily be dependent upon the therapeutic effect to be achieved and may vary with the particular active ingredient, the route of administration, and the age and condition of the individual subject to whom the medicament is to be administered. At times patients may be instructed to take two or any other number of unit dosage forms in a single administration or at times only a portion, such as half or a quarter of the unit dosage form in a single administration.

The dosage form of the invention achieves a balance of performance: tensile strength, stability and fast disintegration. It may be produced by known lyophilisate technology. It can be stored (and packed) in blisters but due to its tensile strength, can also be stored and/or packaged in bottles or bulk. The invention achieves these results in a single processing step, without the need to resort to multiple steps including granulation. Generally, the dosage form of the invention is not in the form of a film, strip, membrane or the like, as such forms will inherently have a comparatively low tensile strength. Instead, it is typically in the form of a tablet, combining tensile strength on the one hand and rapid disintegration in an aqueous medium on the other hand.

In addition to the ingredients previously discussed, the matrix or open matrix network may also include other excipients (auxiliary agents, accessory agents) such as, but not limited to fillers, matrix-forming agents, thickeners, binders, diluents, lubricants, pH adjusting agents, protecting agents, viscosity enhancers, wicking agents, non-effervescent disintegrants, effervescent disintegrants, surfactants, anti-oxidants, wetting agents, colorants, flavouring agents, taste-masking agents, sweeteners, preservatives and so forth.

In one embodiment, a composition of the invention is obtainable by subliming the solvent from a solidified (frozen) liquid preparation comprising an active ingredient, maltodextrin and HA and optionally secondary matrix forming agent(s) in a solvent. Typically, the liquid preparation is placed in a mould, e.g. such that, following solidification and sublimation, a solid composition, typically in a dosage unit, is formed within the mould. The mould can be an open blister pack whereby the solid dosage unit is formed within the blister pack's depression which is thereafter sealed by a sealing film or foil.

In one embodiment, the process comprises introducing unit dosage quantities of said liquid preparation into depressions of an open blister pack; solidifying the unit dosage quantities of the liquid preparation; and then subliming the solvent of the solidified preparation to obtain solid dosage forms within said depressions.

The sublimation can be carried out by freeze drying the solidified liquid preparation comprising the active ingredient, maltodextrin, HA and optionally secondary matrix forming agent(s) in a solvent at low temperature under vacuum. In one embodiment, the solvent is water.

The invention thus discloses a process for preparing fast-disintegrating dosage forms by freeze drying (lyophilizing) a combination of one or more active ingredients, maltodextrin, HA and optionally secondary matrix forming agent(s). The fast-disintegrating dosage form contains a network of the active ingredient and the carriers maltodextrin and HA and optionally the secondary matrix forming agent(s), the network having been obtained by subliming solvent from the solidified liquid preparation that contains the active ingredient, maltodextrin, HA and the other optional matrix forming agents as well as the solvent. Said liquid preparation may be a solution or suspension.

Typically, an initial preparation comprising an active ingredient, maltodextrin, HA and optionally secondary matrix forming agent(s) in a solvent is prepared, followed by solidification and sublimation. The sublimation can be carried out by freeze drying the solidified preparation at low temperature under vacuum.

In a freeze drying procedure, the preparation (in liquid form) that comprises an active ingredient, maltodextrin, HA and any other optional matrix forming agent in a solvent is filled into moulds. Each mould typically contains a defined amount of such preparation with a defined amount of active ingredient. The preparation in the mould is then frozen, for example by passing gaseous cooling medium over the mould. After the preparation has been frozen, the solvent is sublimed therefrom. The sublimation is carried out in a freeze dryer. In consequence, an open matrix network of maltodextrin and HA optionally together with other matrix forming agents, carrying the active ingredient, is thereby formed.

The preparation is contained in a mould during the freeze-drying process to produce a solid form in any desired shape. Prior to the lyophilization, the preparation contained in the mould may be cooled and frozen (e.g. in a fast-freeze tunnel or on the shelves of the lyophilizer), for example using liquid nitrogen or solid carbon dioxide. In one embodiment, the preparation contained in the mould is frozen by lowering the temperature below the solidification temperature at a rate of from 0.1 to 2° C./minute. In another embodiment, the freezing rate is from 0.5 to 1.5° C./minute. In yet another embodiment, the temperature is lowered at a rate of from 10 to 260° C./minute. In another embodiment, the temperature is lowered at a rate of from 20 to 260° C./minute. In a further embodiment, the temperature is lowered at a rate of from 20 to 160° C./minute.

After lyophilization, the freeze dried compositions can either be removed from the mould if desired or stored therein until later use. Typically, each mould is designed so as to produce a unit dosage form of the composition. The composition so obtained is fast-disintegrating and disintegrates within 30 seconds upon contact with an aqueous medium, typically within 10 seconds.

The solvent for preparing the liquid preparation is typically water but may optionally also contain a co-solvent (such as an alcohol, e.g., tert-butyl alcohol) to improve the solubility of the active ingredient.

The liquid preparation may contain a pH adjusting agent to adjust the pH of the composition, when disintegrated in an aqueous medium, within the range of from 2 to 10, typically from 3.5 to 9.5 or from 4.5 to 8. Citric acid, sodium hydroxide, and sodium carbonate can be used as pH adjusting agent, but others including hydrochloric acid and malic acid can also be used. Non-volatile pH adjusting agents will not be removed by freeze drying or other sublimation processes and so may be present in the final product, i.e. in the composition of the present invention.

When preparing a fast-disintegrating dosage form of the invention using the matrix forming agents maltodextrin and HA without adding secondary matrix forming agents, an annealing process (thermal treatment) may be used during the lyophilization process.

The mould may comprise a series of cylindrical or other shape depressions in it, each of a size corresponding to a desired size of a dosage form to be formed.

In one embodiment, the mould is a depression in a sheet of filmic material. The filmic material may contain more than one depression. The filmic material may be similar to that employed in conventional blister packs which are used for packaging oral contraceptive tablets and like medicament forms. For example the filmic material may be made of thermoplastic material with the depressions formed by thermoforming or coldforming. Polyvinyl chloride film can be used as filmic material. Laminates of filmic material may also be used.

EXAMPLES

The invention is further described in the following examples, which are not in any way intended to limit the scope of the inventions as claimed.

A. Materials Used in the Examples Presented Below

| Material | Obtained from |
|---|---|
| Maltodextrin | Roquette Pharma |
| HA (in the form of sodium hyaluronate) | Bio-Technology General Ltd. |
| Desmopressin acetate | Manufactured by Polypeptide Labs A/S, and supplied by Ferring |
| Montelukast Sodium | MSN Pharma |
| Sildenafil citrate | Rakshit Drugs Pvt Ltd |
| Tadalafil | Phalanxiii Labs Pvt Ltd |
| Silodosin | Precise Chemipharma Pvt Ltd |

B. Method for Testing Tensile Strength

Equipment: Engineering Systems (NOT™) Ltd, Model: 5 kN Testing Machine

Procedure: The test parameters for determining tensile strength are entered into the equipment. The parameters include: test speed (15 mm/min), fracture mode, unit (Newton, [N]), fracture percentage (80%), low limit (0.1), and distance between the supporting edges (4.5 mm) A load cell of 10 kg is used and the tensile strength is calculated using the following formula:

$$N/mm^2 = \frac{3 \times \text{Mean Force } (N) \times \text{Distance between two supporting axes in mm}}{2 \times (\text{Thickness in mm})^2 \times (\text{Diameter in mm})}$$

Thickness and diameter are determined using vernier calliper.

C. Method for Testing Disintegration Time (Invitro DT)

This test measures the disintegration time of compositions of the invention in an aqueous medium which is an indication of their disintegration time in saliva.

Equipment: Electrolab, Model: ED2 SAPO

Procedure: The method is followed as per USP 31-NF 26 (General Chapters, <701>Disintegration) and Ph. Eur. 1997 (2.9.1. Disintegration of tablets and capsules). Water is filled into the beaker and maintained at 37° C.±0.5° C. using a water bath. The lyophilisates are placed in a sinker made of copper wire with a diameter of about 0.5 mm (±0.05 mm) and length of about 15 mm. The lyophilisates are then placed into the basket of a basket rack assembly and the instrument is switched on. The disintegration time is noted in seconds.

D. Method for Preparing Placebo Formulation

1) Dissolve required quantity of maltodextrin in 50-60% of total purified water on magnetic/overhead stirrer for 25 minutes,
   Or, for the comparative example,
   add/dissolve levan or pullulan solution under stirring on magnetic stirrer/overhead stirrer;
2) (i) Add required quantity of sodium hyaluronate 1% solution;
   (ii) Add solution of step 1 to solution of step 2(i) under stirring on magnetic stirrer/overhead stirrer;
3) Make up the final volume of the solution using purified water;
4) Mix the solution for 10 minutes on magnetic stirrer/overhead stirrer;
5) Dose the solution into each cavity of preformed blister sheets using positive displacement pipette/dispensing robot;
6) Freeze the filled blisters in freezing tunnel at −60° C. with a residence time of 4 minutes;
7) Optionally transfer the frozen blister from tunnel container to deep freezer maintained at −35° C.;
8) Load frozen blisters on the shelves of lyophilizer maintained at −35° C.;
9) Freeze dry the blisters by ramping from −35° C. to 25° C. at a vacuum of 600 to 120 mTorr;
10) Place the blister sheet containing dried lyophilisates on the punched carrier web of the blister packaging machine to transport the blister sheets through the sealing station of the packaging machine;
11) Seal the blister with a lidding foil and punch into final blisters.

The following formulations were prepared using the method described in the method section "D" above:

Example 1

| Ingredients | Qty per lyophilisate | |
|---|---|---|
| | mg | % w/w |
| Maltodextrin | 30.00 | 98.36 |
| Sodium hyaluronate 1% solution equivalent to sodium hyaluronate | 0.5 | 1.64 |
| Purified water | q.s. to 250 µL | — |
| Total | 30.50 | 100.00 |

Example 2

| Ingredients | Qty per lyophilisate | |
|---|---|---|
| | mg | % w/w |
| Maltodextrin | 25.00 | 97.09 |
| Sodium hyaluronate 1% solution equivalent to Sodium hyaluronate | 0.75 | 2.91 |
| Purified water | q.s. to 250 µL | — |
| Total | 25.75 | 100.00 |

Example 3 (Comparative Example 1)

| Ingredients | Qty per lyophilisate | |
|---|---|---|
| | mg | % w/w |
| Levan | 25.00 | 97.09 |
| Sodium hyaluronate 1% solution equivalent to sodium hyaluronate | 0.75 | 2.91 |
| Purified water | q.s. to 250 µL | — |
| Total | 25.75 | 100.00 |

Example 4 (Comparative Example 2)

| Ingredients | Qty per lyophilisate | |
|---|---|---|
| | mg | % w/w |
| Pullulan | 25.00 | 97.09 |
| Sodium hyaluronate 1% solution equivalent to sodium hyaluronate | 0.75 | 2.91 |
| Purified water | q.s. to 250 µL | — |
| Total | 25.75 | 100.00 |

Example 5 (Comparative Example 3)

| Ingredients | Qty per lyophilisate | |
|---|---|---|
| | mg | % w/w |
| Maltodextrin | 25.00 | 97.09 |
| Levan | 0.75 | 2.91 |
| Purified water | q.s. to 250 µL | — |
| Total | 25.75 | 100.00 |

Example 6 (Comparative Example 4)

| Ingredients | Qty per lyophilisate | |
|---|---|---|
| | mg | % w/w |
| Maltodextrin | 25.00 | 97.09 |
| Pullulan | 0.75 | 2.91 |
| Purified water | q.s. to 250 µL | — |
| Total | 25.75 | 100.00 |

Example 7

A formulation containing desmopressin was prepared according to the method described herein below:

| Ingredients | Qty per lyophilisate | |
|---|---|---|
| | mg | % w/w |
| Desmopressin acetate equivalent to desmopressin | 0.240 | 0.92 |
| Maltodextrin | 25.00 | 96.19 |
| Sodium hyaluronate 1% solution equivalent to sodium hyaluronate | 0.75 | 2.88 |
| Purified water | q.s. to 250 µL | — |
| Total | 25.99 | 100.00 |

Method for Preparing Desmopressin Formulation
1. Dissolve required quantity of maltodextrin in 50-60% of total purified water on magnetic stirrer/overhead stirrer for 25 min;
2. Add required amount of desmopressin acetate under continuous stirring;
3. Add required quantity of sodium hyaluronate 1% solution under continuous stirring;
4. Make up the final volume of the solution using purified water;
5. Mix the solution for 10 min on magnetic stirrer/overhead stirrer;
6. Dose the solution into each cavity of preformed blister sheets using positive displacement pipette/dispensing robot
7. Freeze the filled blisters in freezing tunnel at −60° C. with a residence time of 4 min;
8. Optionally transfer the frozen blister from tunnel container to deep freezer maintained at −35° C.;
9. Load frozen blisters on the shelves of lyophilizer maintained at −35° C.;
10. Freeze dry the blisters by ramping from −35° C. to 25° C. at a vacuum of 600 to 120 mTorr;
11. Place the blister sheet containing dried lyophilisates on the punched carrier web of the blister packaging machine to transport the blister sheets through the sealing station of the packaging machine;
12. Seal the blister with a lidding foil and punch into final blisters.

Example 8

A formulation containing montelukast sodium was prepared according to the method described herein below:

| Ingredients | Qty per lyophilisate | |
|---|---|---|
| | mg | % w/w |
| Montelukast granules equivalent to montelukast (5 mg) | 23.92 | 47.88 |
| Maltodextrin | 25.00 | 50.05 |
| Neotame | 0.08 | 0.16 |
| Cherry flavor | 0.20 | 0.40 |
| Sodium hyaluronate 1% solution equivalent to Sodium hyaluronate | 0.75 | 1.50 |
| Purified water | q.s. to 250 µL | — |
| Total | 49.95 | 100.00 |

Method for Preparing Montelukast Formulation
1. Dissolve required quantity of maltodextrin in 50-60% of total purified water on magnetic stirrer/overhead stirrer for 25 min.
2. Add required amount of neotame and cherry flavor under continuous stirring
3. Add required amount of montelukast granules under continuous stirring
4. Add required quantity of sodium hyaluronate 1% solution under continuous stirring.
5. Make up the final volume of the solution using purified water.
6. Mix the solution for 10 min on magnetic stirrer/overhead stirrer.
7. Dose the solution into each cavity of preformed blister sheets using positive displacement pipette/dispensing robot.
8. Freeze the filled blisters in freezing tunnel at −60° C. with a residence time of 4 min.
9. Optionally transfer the frozen blister from tunnel container to deep freezer maintained at −35° C.
10. Load frozen blisters on the shelves of lyophilizer maintained at −35° C.
11. Freeze dry the blisters by ramping from −35° C. to 25° C. at a vacuum of 600 to 120 mTorr.
12. Place the blister sheet containing dried lyophilisates on the punched carrier web of the blister packaging machine to transport the blister sheets through the sealing station of the packaging machine.
13. Seal the blister with a lidding foil and punch into final blisters.

Example 9

| Ingredients | Qty per lyophilisate | |
|---|---|---|
| | mg | % w/w |
| Sildenafil Citrate equivalen to sildenafil 25 mg | 35.12 | 46.70 |
| Maltodextrin | 40.00 | 53.19 |
| Sodium hyaluronate 1% solution equivalent to sodium hyaluronate | 0.075 | 0.099 |
| Purified water | q.s. to 400 µL | — |
| Total | 75.195 | 100.00 |

Method for Preparing Sildenafil Formulation
1. Dissolve required quantity of maltodextrin in 50-60% of total purified water on magnetic stirrer/overhead stirrer for 5 min;
2. Add required amount of sildenafil citrate under continuous stirring;
3. Add required quantity of sodium hyaluronate 1% solution under continuous stirring;
4. Make up the final volume of the solution using purified water;
5. Mix the solution for 10 min on magnetic stirrer/overhead stirrer;
6. Dose the solution into each cavity of preformed blister sheets using positive displacement pipette/dispensing robot
7. Freeze the filled blisters in freezing tunnel at −60° C. with a residence time of 4 min;
8. Optionally transfer the frozen blister from tunnel container to deep freezer maintained at −35° C.;
9. Load frozen blisters on the shelves of lyophilizer maintained at −35° C.;

10. Freeze dry the blisters by ramping from −35° C. to 25° C. at a vacuum of 600 to 120 mTorr;
11. Place the blister sheet containing dried lyophilisates on the punched carrier web of the blister packaging machine to transport the blister sheets through the sealing station of the packaging machine;
12. Seal the blister with a lidding foil and punch into final blisters.

Example 10

| Ingredients | Qty per lyophilisate | |
|---|---|---|
| | Mg | % w/w |
| Silodosin | 8.0 | 21.01 |
| Maltodextrin | 30.0 | 78.79 |
| Sodium hyaluronate 1% solution equivalent to sodium hyaluronate | 0.075 | 0.19 |
| Purified water | q.s. to 250 µL | — |
| Total | 38.075 mg | 100.00 |

Method for Preparing Silodosin Formulation
1. Dissolve required quantity of maltodextrin in 50-60% of total purified water on magnetic stirrer/overhead stirrer for 5 min;
2. Add required amount of silodosin under continuous stirring;
3. Add required quantity of sodium hyaluronate 1% solution under continuous stirring;
4. Make up the final volume of the solution using purified water;
5. Mix the solution for 10 min on magnetic stirrer/overhead stirrer;
6. Dose the solution into each cavity of preformed blister sheets using positive displacement pipette/dispensing robot
7. Freeze the filled blisters in freezing tunnel at −60° C. with a residence time of 4 min;
8. Optionally transfer the frozen blister from tunnel container to deep freezer maintained at −35° C.;
9. Load frozen blisters on the shelves of lyophilizer maintained at −35° C.;
10. Freeze dry the blisters by ramping from −35° C. to 25° C. at a vacuum of 600 to 120 mTorr;
11. Place the blister sheet containing dried lyophilisates on the punched carrier web of the blister packaging machine to transport the blister sheets through the sealing station of the packaging machine;
12. Seal the blister with a lidding foil and punch into final blisters.

Example 11

| Ingredients | Qty per lyophilisate | |
|---|---|---|
| | Mg | % w/w |
| Tadalafil | 10.0 | 24.95 |
| Maltodextrin | 30.0 | 74.85 |
| Sodium hyaluronate 1% solution equivalent to sodium hyaluronate | 0.075 | 0.187 |
| Purified water | q.s. to 250 µL | — |
| Total | 40.075 mg | 100.00 |

Method for Preparing Tadalafil Formulation
1. Dissolve required quantity of maltodextrin in 50-60% of total purified water on magnetic stirrer/overhead stirrer for 5 min;
2. Add required amount of tadalafil under continuous stirring;
3. Add required quantity of sodium hyaluronate 1% solution under continuous stirring;
4. Make up the final volume of the solution using purified water;
5. Mix the solution for 10 min on magnetic stirrer/overhead stirrer;
6. Dose the solution into each cavity of preformed blister sheets using positive displacement pipette/dispensing robot
7. Freeze the filled blisters in freezing tunnel at −60° C. with a residence time of 4 min;
8. Optionally transfer the frozen blister from tunnel container to deep freezer maintained at −35° C.;
9. Load frozen blisters on the shelves of lyophilizer maintained at −35° C.;
10. Freeze dry the blisters by ramping from −35° C. to 25° C. at a vacuum of 600 to 120 mTorr;
11. Place the blister sheet containing dried lyophilisates on the punched carrier web of the blister packaging machine to transport the blister sheets through the sealing station of the packaging machine;
12. Seal the blister with a lidding foil and punch into final blisters.

The tensile strength and in-vitro DT for the formulations prepared according to Examples 1 to 11 are presented in Table 1.

TABLE 1

| Example No | Tensile strength (N/mm$^2$) | In-vitro DT (sec) |
|---|---|---|
| 1 | 0.37 | 20 |
| 2 | 0.21 | 6 |
| 3 | 0.34 | >60 |
| 4 | Hard and elastic | >60 |
| 5 | 0.05 | 2 |
| 6 | 0.04 | 2 |
| 7 | 0.16 | 2 |
| 8 | 0.22 | 4 |
| 9 | 0.10 | 5 |
| 10 | 0.12 | 4 |
| 11 | 0.15 | 4 |

The invention claimed is:
1. A pharmaceutical composition comprising an open matrix network carrying one or more pharmaceutically active ingredients, wherein the open matrix network is a matrix of water-soluble or water-dispersible carrier material having interstices dispersed throughout and comprises maltodextrin and hyaluronic acid or a pharmaceutically acceptable salt thereof, wherein the maltodextrin constitutes 40 to 99% by weight of the open matrix network and material carried by the open matrix network, based on the total weight of the open matrix network and material carried by the open matrix network, and wherein the pharmaceutical composition disintegrates in an aqueous medium within 30 seconds.

2. The pharmaceutical composition according to claim 1, wherein the hyaluronic acid has an average molecular weight in the range from $1\times10^4$ to $1\times10^7$ dalton.

3. The pharmaceutical composition according to claim 1, having a tensile strength of at least 0.1 N/mm$^2$.

4. The pharmaceutical composition according to claim 1, wherein the open matrix network and material carried by open matrix network comprise 40 to 99% by weight maltodextrin and 0.99 to 5% by weight hyaluronic acid or a pharmaceutically acceptable salt thereof, based on the total weight of the open matrix network and material carried by the open matrix network.

5. The pharmaceutical composition according to claim 1, wherein the open matrix network and material carried by the open matrix network comprise 50 to 98% by weight maltodextrin and 0.99 to 3% by weight hyaluronic acid or a pharmaceutically acceptable salt thereof, based on the total weight of the open matrix network and material carried by the open matrix network.

6. The pharmaceutical composition according to claim 1, wherein the composition disintegrates in an aqueous medium within 10 seconds.

7. The pharmaceutical composition according to claim 1, which is in an oral dosage form.

8. The pharmaceutical composition according to claim 7, which is adapted for sublingual administration.

9. The pharmaceutical composition according to claim 1, wherein the active ingredient is desmopressin, desmopressin acetate, montelukast, montelukast sodium, sildenafil, sildenafil citrate, silodosin or tadalafil.

10. The pharmaceutical composition according to claim 1, obtained by a process comprising subliming solvent from a solidified liquid preparation comprising the active ingredient, maltodextrin and hyaluronic acid or a pharmaceutically acceptable salt thereof in a solvent.

11. A pharmaceutical composition prepared by a process comprising:
(a) preparing a liquid preparation comprising maltodextrin, hyaluronic acid or a pharmaceutically acceptable salt thereof, and one or more active ingredients in a solvent;
(b) freezing said liquid preparation to obtain a frozen preparation; and
(c) subliming the solvent from the frozen preparation to obtain a pharmaceutical composition,
wherein the pharmaceutical composition comprises 40 to 99% by weight maltodextrin, and
wherein the pharmaceutical composition disintegrates within 30 seconds upon contact with an aqueous medium.

* * * * *